US012282017B1

United States Patent
Gao et al.

(10) Patent No.: US 12,282,017 B1
(45) Date of Patent: Apr. 22, 2025

(54) HP SPHERICAL DEFORMATION DIAGNOSIS MODEL AND CONSTRUCTION METHOD THEREOF

(71) Applicant: SHANGHAI OUTDO BIOTECH CO., LTD., Shanghai (CN)

(72) Inventors: Hengjun Gao, Shanghai (CN); Zishao Zhong, Shanghai (CN); Xin Wang, Shanghai (CN); Xiaoyan Zhang, Shanghai (CN); Jingjing Liu, Shanghai (CN)

(73) Assignee: SHANGHAI OUTDO BIOTECH CO., LTD., Shanghai (CN)

( * ) Notice: Subject to any disclaimer, the term of this patent is extended or adjusted under 35 U.S.C. 154(b) by 0 days.

(21) Appl. No.: 18/846,648

(22) PCT Filed: Aug. 9, 2022

(86) PCT No.: PCT/CN2022/111035
§ 371 (c)(1),
(2) Date: Sep. 12, 2024

(87) PCT Pub. No.: WO2023/231176
PCT Pub. Date: Dec. 7, 2023

(30) Foreign Application Priority Data

May 30, 2022 (CN) .......................... 202210595882.5

(51) Int. Cl.
*G06V 10/776* (2022.01)
*G01N 33/569* (2006.01)
(Continued)

(52) U.S. Cl.
CPC ......... *G01N 33/56922* (2013.01); *G06T 5/20* (2013.01); *G06T 5/50* (2013.01);
(Continued)

(58) Field of Classification Search
None
See application file for complete search history.

(56) References Cited

U.S. PATENT DOCUMENTS

| 10,304,193 B1 | 5/2019 | Wang et al. |
| 2021/0005308 A1 | 1/2021 | Klaiman |

FOREIGN PATENT DOCUMENTS

| CN | 109003659 A | 12/2018 |
| CN | 110660477 A | 1/2020 |

(Continued)

OTHER PUBLICATIONS

Che, Shuanlong, et al. "Morphological Detection Of Helicobector Pyloric Organisms On Gastric Mucosa Using Deep Learning Of The Artificial Intelligence." (2018). (Year: 2018).*

*Primary Examiner* — Samah A Beg
(74) *Attorney, Agent, or Firm* — Bayramoglu Law Offices LLC (57) ABSTRACT

An HP spherical deformation diagnosis model and a construction method thereof are provided. The HP spherical deformation diagnosis model is used for identifying whether HP spherical deformation exists in an IHC dyeing image of an HP positive gastric mucosal sample, and includes: an image processing module and an identification module; the image processing module comprises a contrast enhancement module, an image filtering module, and an HP dyeing extraction module; the contrast enhancement module comprises: an HIS color model transformation module, which is used for transforming an original image from an RGB color model to an HIS color model in which hue, saturation, and intensity are separated; and a piecewise linear transformation module, which is used for enhancing a grayscale region of interest in the image by using a piecewise linear trans-
(Continued)

formation method for a brightness component in the HIS color module, so as to improve the image.

13 Claims, 7 Drawing Sheets

(51) Int. Cl.

| | |
|---|---|
| *G06T 5/20* | (2006.01) |
| *G06T 5/50* | (2006.01) |
| *G06T 5/60* | (2024.01) |
| *G06T 5/94* | (2024.01) |
| *G06T 7/00* | (2017.01) |
| *G06T 7/11* | (2017.01) |
| *G06T 7/155* | (2017.01) |
| *G06T 7/90* | (2017.01) |
| *G06V 10/30* | (2022.01) |
| *G06V 10/34* | (2022.01) |
| *G06V 10/36* | (2022.01) |
| *G06V 10/56* | (2022.01) |
| *G06V 10/764* | (2022.01) |
| *G06V 10/82* | (2022.01) |
| *G06V 10/94* | (2022.01) |
| *G06V 20/69* | (2022.01) |
| *G16H 30/40* | (2018.01) |
| *G16H 50/20* | (2018.01) |

(52) U.S. Cl.
CPC .................. *G06T 5/60* (2024.01); *G06T 5/94* (2024.01); *G06T 7/0014* (2013.01); *G06T 7/11* (2017.01); *G06T 7/155* (2017.01); *G06T 7/90* (2017.01); *G06V 10/30* (2022.01); *G06V 10/34* (2022.01); *G06V 10/36* (2022.01); *G06V 10/56* (2022.01); *G06V 10/764* (2022.01); *G06V 10/776* (2022.01); *G06V 10/82* (2022.01); *G06V 10/94* (2022.01); *G06V 20/695* (2022.01); *G06V 20/698* (2022.01); *G16H 30/40* (2018.01); *G16H 50/20* (2018.01); *G01N 2469/10* (2013.01); *G06T 2207/10024* (2013.01); *G06T 2207/10056* (2013.01); *G06T 2207/20028* (2013.01); *G06T 2207/20036* (2013.01); *G06T 2207/20081* (2013.01); *G06T 2207/20084* (2013.01); *G06T 2207/30024* (2013.01)

(56) References Cited

FOREIGN PATENT DOCUMENTS

| | | |
|---|---|---|
| CN | 111489369 A | 8/2020 |
| CN | 111861975 A | 10/2020 |
| CN | 114678121 A | 6/2022 |

\* cited by examiner

Firstly initialize RPN network parameters using the previous model, and train the RPN network end-to-end to fine-tune the RPN network.

↓

Initialize Faster R-CNN network parameters using the previous model; and train the Faster R-CNN network based on the target proposal box generated by RPN.

↓

Initialize RPN network parameters using a Faster R-CNN network, and fix the shared convolution layer with only the specific RPN network layer being fine-tuned.

↓

Maintain a shared convolution layer, and fine-tune the full connection layer of the Faster R-CNN network.

FIG. 7

China Helicobacter Pylori
Molecular Medical Center

Pathological examination report

Barcode No.: C10100000017      Pathological No.: 2100840

| | | |
|---|---|---|
| Name: Meng X | Sex: Female | Age: 44 |
| Request Hospital: Anhui No. 2 People's Hospital | Outpatient/Hospitalization No.: Request Doctor: Cheng XX | Specimen Type: gastric mucos Sampling Date: |
| Request Department: Clinical diagnosis: | Sample Condition: no abnormality observed by naked eye | Date of Receipt: 2021-03-05 |

Visible to the naked eye: two tissue to be tested, 0.1 x 0.1 x 0.1 cm and 0.2 x 0.1 x 0.1 cm in size, off-white, medium in quality.

Visible under microscope:

IHC results: positive (+)

IHC instructions: about 40% of the HP cells are spherical under microscope.

Tested by: Li X      Reviewed by: Yan XX      Report date: 2021/03/10

Comments:
1: this test report is only responsible for this sample. For clinician reference only.
2: The test was entrusted to Shanghai Outdo Clinic Co., Ltd. If in doubt, please contact 021-20790358.

HP SPHERICAL DEFORMATION DIAGNOSIS MODEL AND CONSTRUCTION METHOD THEREOF

CROSS REFERENCE TO THE RELATED APPLICATIONS

This application is the national phase entry of International Application No. PCT/CN2022/111035, filed on Aug. 9, 2022, which is based upon and claims priority to Chinese Patent Application No. 202210595882.5, filed on May 30, 2022, the entire contents of which are incorporated herein by reference.

TECHNICAL FIELD

The present invention relates to the field of medical image recognition, and in particular to an HP spherical deformation diagnosis model and construction method thereof to enable artificial intelligence to identify and interpret *Helicobacter pylori* infection and spherical deformation.

BACKGROUND

*Helicobacter pylori* (HP) undergoes spherical deformation after treatment failure, which is also an important reason for the failure of *Helicobacter pylori* eradication treatment. However, few hospitals carry out the *Helicobacter pylori* spherical deformation diagnosis. This is because currently, the *Helicobacter pylori* spherical deformation diagnosis requires immunohistochemical staining followed by radiographic diagnosis by a specialized pathologist. However, the small number of pathologists in China and the varying levels of pathologists in primary hospitals make it impossible to carry out such programs.

The pathological section is a two-dimensional medical image, which is typical structured data with the possibility of deep learning suitable for artificial intelligence (AI). Patent CN111489369 A deeply learns to identify and locate *Helicobacter pylori* in the target section after immunohistochemical staining through artificial intelligence, but it cannot determine whether HP has a spherical deformation.

SUMMARY

In view of the above-mentioned deficiencies of the prior art, the object of the present invention is to provide a rapid, reliable, and easy-to-use tool for the HP spherical deformation diagnosis in clinical practice, to greatly reduce the technical threshold for HP spherical deformation diagnosis, to reduce the diagnosis time, to improve the accuracy and consistency of diagnosis, to guide the clinical practice of HP personalized precise treatment, and to accelerate the development and promotion of HP personalized precise treatment.

Disclosed is a construction method for an HP spherical deformation diagnosis model, including the following steps:
S1, taking several immunochemical staining images having *Helicobacter pylori* (HP) spherical deformation as a training set and a validation set respectively;
S2, manually labeling *Helicobacter pylori* morphology in the training set;
S3, subjecting the images in the training set to contrast enhancement, image filtering, and HP staining extraction operations; wherein the contrast enhancement includes firstly transforming an original image from a red, green, blue (RGB) color model to a hue-intensity-saturation (HIS) color model in which hue, saturation, and intensity are separated, and then using a piecewise linear transformation method on the obtained brightness component;
the piecewise linear transformation method includes substituting Eq. 1-1 into Eq. 1-2, in the case where X, min and max are known, calculating Y to obtain a large number of Y corresponding to X, and plotting X and Y as horizontal and vertical coordinates to obtain two pairs of turning points (X1, Y1) and (X2, Y2); enhancing the grayscale region of interest in the image by the piecewise linear transformation method, i.e. stretching to the (0, 1) interval, thereby improving the image;

$$k=1/(\max-\min) \qquad \text{Eq. 1-1}$$

$$Y=k(X-\min) \qquad \text{Eq. 1-2}$$

wherein k is the stretching coefficient; max and min are 4-6% of the pixel value of the point with the highest pixel value on the original image and 4-6% of the pixel value of the point with the lowest pixel value on the original image, respectively; X is the color hue saturation of the original image; and Y is the color hue saturation of the adjusted image;
the image filtering adopts bilateral filtering technology to filter the improved image processed by the piecewise linear transformation method;
the HP staining extraction adopts a deconvolution algorithm to enhance the DAB staining information about the image after the image filtering processing, suppress other staining information, and transform the same into grey levels according to the amount of DAB staining, so as to obtain an image for AI identification;
S4, training a U-Net neural network with the image for AI identification;
S5, performing k-fold cross-validation and optimization to obtain the HP spherical deformation diagnosis model;
S6, performing HP spherical deformation identification on the image in the validation set using the HP spherical deformation diagnosis model, and performing consistency comparison with a manual interpretation result; when the consistency reaches above 70%, the HP spherical deformation diagnosis model is successfully constructed.

In some embodiments, max and min are 5% of the pixel value of the point with the highest pixel value on the original image and 5% of the pixel value of the point with the lowest pixel value on the original image, respectively; X1 is 0.25-0.32; Y1 is 0.11-0.14; X2 is 0.83-0.88; and Y2 is 0.90-0.99.

In some embodiments, the deconvolution algorithm adopted in step S3 is a color deconvolution technique, involving the following Eqs.: Eq. 2-2, Eq. 2-3, Eq. 2-4, and Eq. 2-5;

$$OD_c=-\log_{10}(I_c/I_{o,c})=A \times C_c \qquad \text{Eq. 2-2}$$

$$\varphi_c=\exp(-S\varphi_c') \qquad \text{Eq. 2-3}$$

$$\varphi_c'=D\theta_c \qquad \text{Eq. 2-4}$$

$$\varphi_c=10^{-ODc} \qquad \text{Eq. 2-5}$$

where A represents the action amount of the stain; $I_{o,c}$ represents the intensity of the incident light; $I_c$ represents the intensity of the light after passing through the sample, and subscript c represents the detected channel; $C_c$ represents the light absorption factor; $OD_c$ represents the optical density; $\varphi_c$ represents the red, green and blue optical density function of each pixel; $\varphi_c'$ represents the red, green and blue optical density function of each pixel newly defined by staining with stained tissue sections; S represents the matrix composed of the absorption factors respectively corresponding to the three channels of RGB of each stain; and D is the inverse matrix of S; and $\theta_c = -\log(\varphi_c)$;

in the case where S, A and $C_c$ are known, $OD_c$ is calculated by Eq. 2-2; $\varphi_c$ is calculated by Eq. 2-5; $\varphi_c'$ is calculated by Eq. 2-3; $\theta_c$ is calculated by $\theta_c = -\log(\varphi_c)$; D is calculated by substituting $\varphi_c'$ and $\theta_c$ into Eqs. 2-4; and D is a 3×3 matrix composed of the staining amount of hematoxylin, eosin and DAB staining in an RGB space after the deconvolution algorithm; the DAB staining amount in the D matrix is taken and transformed into a grey level to obtain the image for AI identification.

In some embodiments, the immunochemical staining image in step S1 is one or more selected from the group consisting of immunocytochemistry (ICC) staining image and immunohistochemistry (IHC) staining image.

In some embodiments, the ICC staining image in step S1 is derived from an ICC staining mapping performed after spherical deformation induction treatment of standard HP strain 26695; the standard HP strain 26695 spherical deformation induction treatment specifically includes: allowing standard HP strain 26695 to grow on a polylysine treated coverslip, after successful deformation with amoxicillin antibiotic solution at 0.02-0.04 g/ml (1/2 MIC), discarding the culture medium, and incubating the HP strain in 3%-5% (preferably 4%) paraformaldehyde at room temperature for 10-15 minutes (preferably 10 minutes);

the IHC staining image in step S1 is derived from an IHC staining mapping performed after processing the HP positive gastric mucosa sample; the processing of the HP positive gastric mucosa sample specifically includes fixing the isolated HP positive gastric mucosa samples in 4% paraformaldehyde for 24 hours, then dehydrating, embedding, and sectioning to prepare a paraffin section. Gradient dewaxing was performed (xylene once→xylene again→95% ethanol once→95% ethanol again→75% ethanol once→75% ethanol again, 2 min each).

In some embodiments, step S2 specifically includes: using LabelImg software to label HP morphology in the ICC staining image and/or the IHC staining image according to four types: rod, rod cross-section, sphere, and aggregation, wherein the diameter of the sphere is 2-3 times the diameter of the adjacent rod, labeling all HP intermediate morphology as spherical wherein the HP intermediate morphology refers to the morphology of *Helicobacter pylori* during the deformation from rod to sphere; labeling the rod, the rod cross-section, and the aggregation as non-spherical wherein the aggregation means that the HPs are aggregated together and the morphology cannot be clearly distinguished.

In some embodiments, step S4 specifically includes: training the U-Net neural network using a Faster region-based convolutional neural network (R-CNN) algorithm on the image for AI identification; and adopting VGG16 as a base network model for the Faster R-CNN algorithm.

In some embodiments, the training set contains thousands of immunochemical staining images; the validation set contains hundreds of immunochemical staining images.

Further, the training set contains 8-10 times more immunochemical staining images than the validation set.

Further, the training set contains 3500 ICC staining images and 1000 IHC staining images; the validation set contains 500 IHC staining images.

The present invention also discloses a construction system for an HP spherical deformation diagnosis model for identifying whether HP spherical deformation exists in an IHC staining image of an HP positive gastric mucosal sample and/or an HP strain ICC staining image, including an image processing module and an identification module; wherein the image processing module includes a contrast enhancement module, an image filtering module, and an HP staining extraction module;

the contrast enhancement module includes:
an HIS color model transformation module configured to transform an original image from an RGB color model to an HIS color model in which hue, saturation, and intensity are separated; and
a piecewise linear transformation module configured to enhance a grayscale region of interest in the image by using a piecewise linear transformation method for a brightness component in the HIS color module, so as to improve the image;
the piecewise linear transformation method includes substituting Eq. 1-1 into Eq. 1-2, in the case where X, min and max are known, calculating Y to obtain a large number of Y corresponding to X, and plotting X and Y as horizontal and vertical coordinates to obtain two pairs of turning points (X1, Y1) and (X2, Y2); enhancing the grayscale region of interest in the image by the piecewise linear transformation method, i.e. stretching to the (0, 1) interval, thereby improving the image;

$$k = 1/(\max - \min) \qquad \text{Eq. 1-1}$$

$$Y = k(X - \min) \qquad \text{Eq. 1-2}$$

wherein k is the stretching coefficient; max and min are 4-6% of the pixel value of the point with the highest pixel value on the original image and 4-6% of the pixel value of the point with the lowest pixel value on the original image, respectively; X is the color hue saturation of the original image; and Y is the color hue saturation of the adjusted image;
the image filtering module adopts bilateral filtering technology to filter the improved image processed by the piecewise linear transformation method;
the HP staining extraction module adopts a deconvolution algorithm to enhance the DAB staining information about the image after the image filtering processing, suppress other staining information, and transform the same into grey levels according to the amount of DAB staining, so as to obtain an image for AI identification;
the identification module is configured to identify the image for AI identification, and make an interpretation of whether an HP spherical deformation exits.

In some embodiments, max and min are 5% of the pixel value of the point with the highest pixel value on the original image and 5% of the pixel value of the point with the lowest pixel value on the original image, respectively; X1 is 0.25-0.32; Y1 is 0.11-0.14; X2 is 0.83-0.88; and Y2 is 0.90-0.99.

In some embodiments, the system is further configured to give the proportion of IHC staining image of the HP positive gastric mucosal sample and/or the HP strain ICC staining image; the identification module, when identifying the image for AI identification, is also capable of giving the proportion of IHC staining image of the HP positive gastric mucosal sample and/or the HP strain ICC staining image.

In some embodiments, the deconvolution algorithm used by the HP staining extraction module is a color deconvolution technique, involving the following Eqs.: Eq. 2-2, Eq. 2-3, Eq. 2-4, and Eq. 2-5;

$$OD_c = -\log_{10}(I_c/I_{o,c}) = A \times C_c \qquad \text{Eq. 2-2}$$

$$\varphi_c = \exp(-S\varphi_c') \qquad \text{Eq. 2-3}$$

$$\varphi_c' = D\theta_c \qquad \text{Eq. 2-4}$$

$$\varphi_c = 10^{-ODc} \qquad \text{Eq. 2-5}$$

where A represents the action amount of the stain; $I_{o,c}$ represents the intensity of the incident light; $I_c$ represents the intensity of the light after passing through the sample, and subscript c represents the detected channel; $C_c$ represents the light absorption factor; $OD_c$ represents the optical density; $\varphi_p$ represents the red, green and blue optical density function of each pixel; $\varphi_c'$ represents the red, green and blue optical density function of each pixel newly defined by staining with stained tissue sections; S represents the matrix composed of the absorption factors respectively corresponding to the three channels of RGB of each stain; and D is the inverse matrix of S; and $\theta_c = -\log(\varphi_c)$;

in the case where S, A and $C_c$ are known, $OD_c$ is calculated by Eq. 2-2; $\varphi_c$ is calculated by Eq. 2-5; $\varphi_c'$ is calculated by Eq. 2-3; 6, is calculated by $\theta_c = -\log(\varphi_c)$; D is calculated by substituting $\varphi_c'$ and $\theta_c$ into Eqs. 2-4; and D is a 3×3 matrix composed of the staining amount of hematoxylin, eosin and DAB staining in an RGB space after the deconvolution algorithm; the DAB staining amount in the D matrix is taken and transformed into a grey level to obtain the image for AI identification.

The present invention also discloses a computer-readable storage medium having stored thereon executable instructions that, when executed, implement the piecewise linear transformation module of the construction system for the HP spherical deformation diagnosis model as described above.

In some embodiments, the executable instructions, when executed, further implement the functions of the HP staining extraction module of the construction system for the HP spherical deformation diagnosis model as described above.

In some embodiments, the executable instructions, when executed, further implement the functions of the construction system for the HP spherical deformation diagnosis model as described above.

The present invention also discloses a terminal comprising:

a memory configured to store executable instructions;

a processor configured to, when executing the executable instructions stored in the memory, implement the piecewise linear transformation module of the construction system for the HP spherical deformation diagnosis model as described above.

In some embodiments, the processor, when executing the executable instructions stored in the memory, further implements the functions of the HP staining extraction module of the construction system for the HP spherical deformation diagnosis model as described above.

In some embodiments, the processor, when executing the executable instructions stored in the memory, further implements the functions of the construction system for the HP spherical deformation diagnosis model as described above.

The present invention employs artificial intelligence deep learning algorithms for target identification of spherical deformation of *H. pylori* bacteria, which may eliminate the need to set up or train pathologists at a sub-center. According to the present application, the diagnosis work of the HP spherical deformation is given to a computer, such that the technical threshold of the spherical deformation diagnosis is greatly reduced, the time required for the diagnosis is shortened, errors caused by uneven levels of pathologists are reduced, the diagnosis accuracy and consistency are improved, and accelerate the popularization of *Helicobacter pylori* spherical deformation diagnosis.

The conception, the specific structure and the technical effects of the present invention will be further described with reference to the accompanying drawings, so that the objects, features and effects of the present invention can be fully understood.

DETAILED DESCRIPTION OF THE EMBODIMENTS

In order to make the technical means, creative features, purpose and efficacy of the present invention easy to understand, the present invention is further described in combination with specific illustrations. But the present invention is not limited to the following embodiments.

It should be noted that the structure, proportion, size, etc. shown in the accompanying drawings in this specification are only for the purpose of cooperating with the content disclosed in the specification, for the understanding and reading of those familiar with this technology, and are not intended to limit the conditions under which the present invention can be implemented. Therefore, they do not have any substantive technical meaning. Any modification of the structure, change in the proportion relationship, or adjustment of the size should still fall within the scope of the technical content disclosed in the present invention without affecting the efficacy and objectives that can be achieved by the present invention.

Meanwhile, the terms "upper", "lower", "left", "right" and "a" cited in the present specification are merely for convenience of description and are not intended to limit the scope of the present invention, and changes or modifications in the relative terms may be made without materially changing the technical contents.

Figure 1:
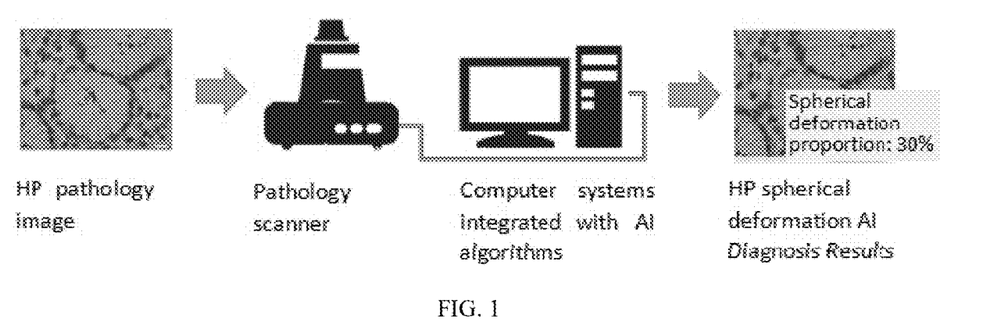
FIG. 1 is a flow chart for identifying an HP spherical deformation by an HP spherical deformation diagnosis model according to the present invention.
Figure 2:
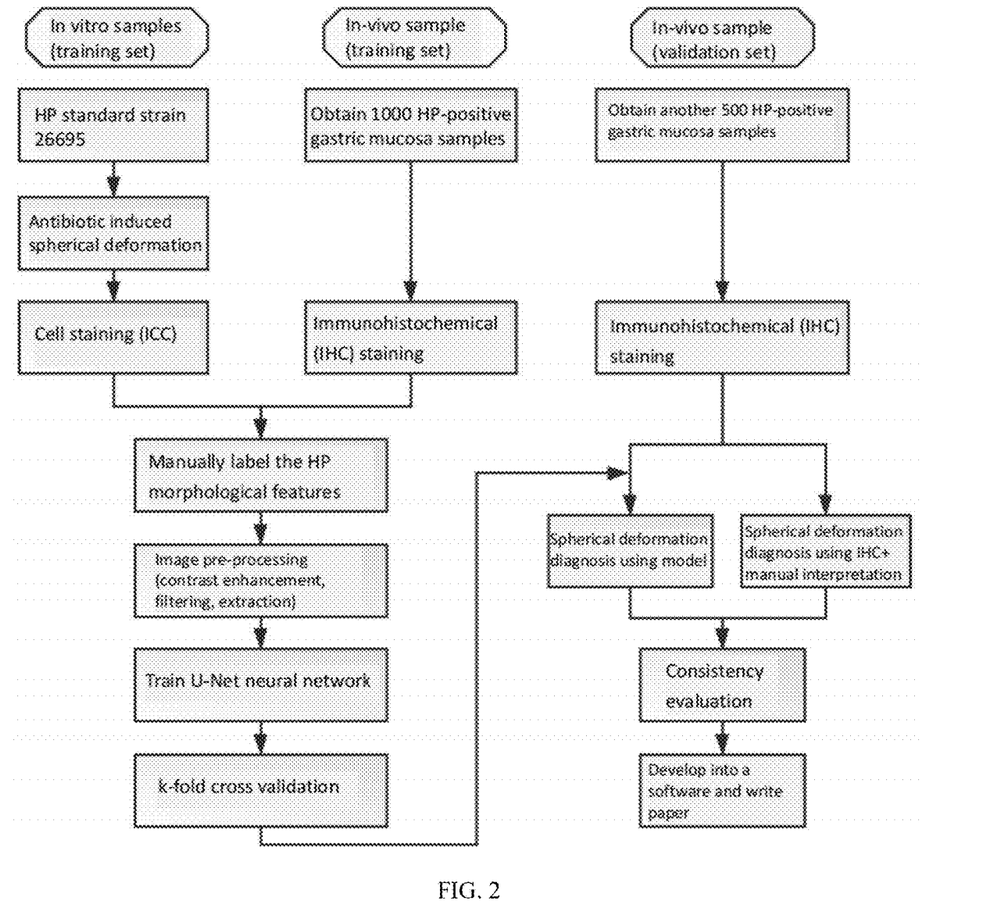
FIG. 2 is a block flow diagram of a construction method for an HP spherical deformation diagnosis model according to the present invention.

FIG. 1 shows a flow chart for identifying an HP spherical deformation by an HP spherical deformation diagnosis model according to the present invention. The computer system incorporating the artificial intelligence algorithm of FIG. 1 is a vehicle for the HP spherical deformation diagnosis model of the present invention. FIG. 2 shows a general flow of a construction method for an HP spherical deformation diagnosis model according to the present invention. The present invention will be summarized with reference to FIGS. 1 and 2: In an HP microaerophilic culture platform, sub-dose antibiotics can be used to induce the HP spherical deformation of HP strains, and immunocytochemical staining can be performed to construct 3500 pictures of the HP spherical deformation. In addition, 1000 HP positive gastric mucosa samples can be collected for HP immunohistochemical staining. The obtained immunochemical staining (including immunocytochemical staining and immunohistochemical staining) pictures can be used for morphological classification and labeling by pathologists using the LabelImg software.

After pretreatment such as contrast enhancement (HSI color model+piecewise linear transformation), filtering (bilateral filtering), and color deconvolution extraction, the labeled immunochemical staining image can be divided into several sub-images which can be overlapped with each other, and the sample size is expanded using inversion, translation, folding and data enhancement method based on GAN. Using the pre-processed samples as the training set, the U-Net neural network can be trained to accurately identify and segment the position and boundary of HP in the image, and calculate the occurrence proportion of spherical deformation.

The raw data can be subjected to k-fold cross-validation, and the samples can be randomly divided into k groups. Each time (k-1) groups can be selected as a training set, the remaining 1 can be used as a test set. The cross-validation can be repeated k times, and the average of the accuracy of k times can be taken as the evaluation index of the final model.

In addition, by introducing the idea of reinforcement learning, medical experts can label the areas of misclassification obtained by machine training, thus obtaining a prompt graph. The AI that receives the feedback information can re-learn and adjust the parameters of the spherical deformation segmentation network on the basis of the original picture and the probability graph obtained from the previous training combined with the newly obtained prompt graph. By repeating the above steps, AI can ultimately more accurately identify areas that are difficult to distinguish under conventional methods.

In order to prevent the over-fitting phenomenon, the present invention divides the overall sample into a training set and a validation set and determines optimal model parameters through the performance of the model on the validation set. The overall samples included 3500 pictures of HP standard strain 26695 and 1500 corresponding pictures of 1500 HP positive gastric mucosa samples (1 picture for each sample). Among them, 500 pictures of HP positive gastric mucosa samples can be taken as a validation set, and the remaining 4500 pictures can be taken as the training set.

In the total samples, the HP immunohistochemical pictures of 500 clinical samples (500 pictures of HP positive gastric mucosa samples) obtained in the later period can be used as the validation set, and the consistency evaluation of the model for artificial intelligence diagnosis of HP spherical deformation constructed in the training set and the IHC+ artificial interpretation for spherical deformation diagnosis can be conducted. The consistency of the artificial intelligence diagnosis results and the artificial interpretation results can reach 73.3%, proving that the artificial intelligence diagnosis is reliable. Then the software was developed and the paper was written. The method and system involved in this model are conducive to reducing the technical threshold of HP spherical deformation diagnosis, reducing the diagnosis time, improving the accuracy and consistency of diagnosis, guiding the clinical implementation of HP personalized precise treatment, and promoting the development of HP personalized precise treatment.

The above was made into a database format to create a system software by using software algorithms. Then, pathologists can scan the immunohistochemistry samples with pathological instruments for image collection, and use artificial intelligence algorithms to conduct comprehensive analysis and generate reports on the computer.

Example 1

Figure 9:
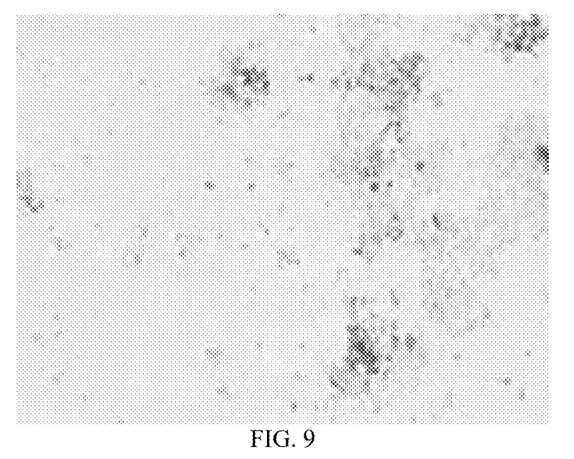
FIG. 9 is an ICC image of HP standard strain 26695 after spherical deformation induction.

1. Immunochemical Staining [ICC and IHC]
   (1) Bacterial Sample Treatment: standard HP strain 26695 (purchased from the US ATCC cell bank) was grown on a polylysine-treated coverslip. After successful induction of spherical deformation with an antibiotic solution (amoxicillin) at 1/2 MIC concentration (minimum inhibitory concentration), the culture medium was discarded and incubated in 4% paraformaldehyde (in PBS, pH 7.4) for 10 min at room temperature.
   (2) Tissue Sample Treatment: samples of gastric mucosa obtained in vitro were fixed in 4% paraformaldehyde for 24 hours, dehydrated conventionally, embedded, and sectioned to prepare a paraffin section. Gradient dewaxing was performed (xylene once→xylene again→95% ethanol once→95% ethanol again→75% ethanol once→75% ethanol again, 2 min each).
   (3) Immunochemical staining: according to the instructions of the HP immunohistochemistry kit (Fuzhou Maixin Biotechnology Development Co. Ltd.), the treated bacterial samples and tissue samples were subjected to ICC staining and IHC staining, respectively.
   ①ICC Staining (FIG. 9)
   The steps are as follows: fixing bacteria in formalin for 30 min→washing three times with phosphate buffered saline (PBS)→permeabilizing→washing three times with PBS-→blocking with endogenous peroxidase blocker→incubating primary antibody (MAB-0692 murine monoclonal antibody)→rewarming (to room temperature)→washing three times with PBS→incubating secondary antibody (adding enzyme-labeled goat anti-mouse/rabbit IgG polymer)→washing three times with PBS solution→observing under a microscope (adding 50% PBS+50% glycerol dropwise on a glass slide).
   ②IHC Staining
   The steps are as follows: dewaxing and hydration→antigen retrieval (EDTA retrieval solution)→blocking endogenous peroxidase→adding antibody→adding enzyme-labeled goat anti-mouse/rabbit IgG polymer→developing→re-staining→dehydration, transparency processing, sealing→biological microscopic reading→result determination.

The main reagents used in ① and ② above (such as MAB-0692 mouse monoclonal antibody, enzyme-labeled goat anti-mouse/rabbit IgG polymer, endogenous peroxidase blocker, etc.) are from the HP immunohistochemistry kit (Fuzhou Maixin Biotechnology Development Co. Ltd.).

2. HP Morphological Labeling

Figure 3:
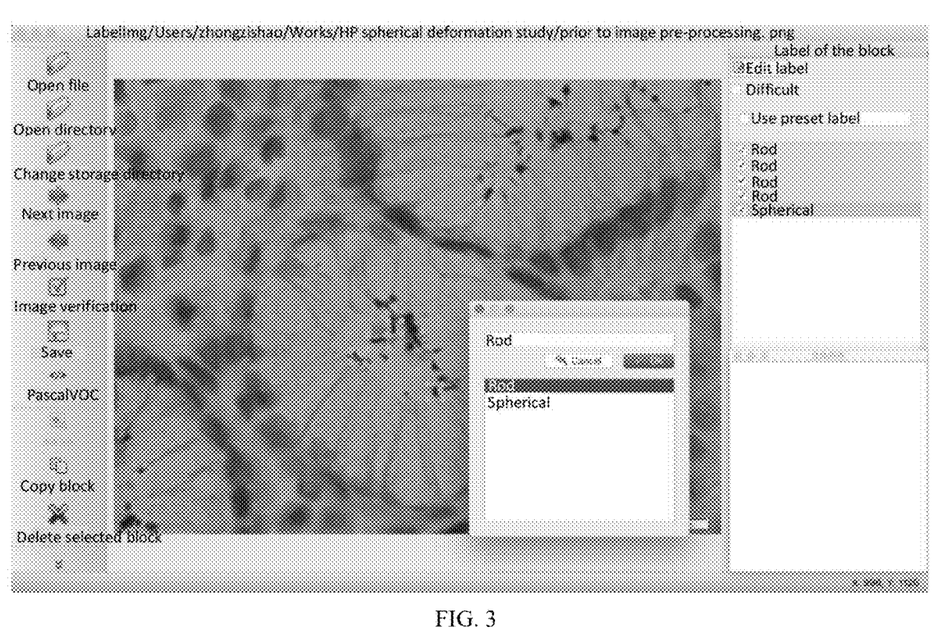
FIG. 3 is a labeling illustration of the LabelImg software.
Figure 10:
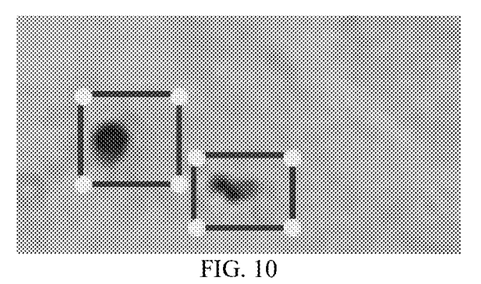
FIG. 10 is an electron micrograph of HP rod (right) and sphere (left) morphologies.
Figure 11:
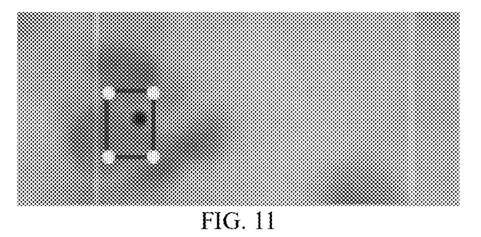
FIG. 11 is an electron micrograph of the HP rod cross-sectional morphology.
Figure 12:
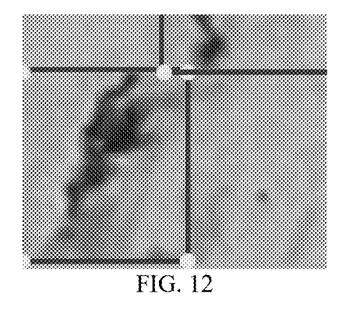
FIG. 12 is an electron micrograph of the HP aggregation morphology.

HP morphology labeling (FIG. 3) was performed by 2 pathologists using LabelImg software to label HP morphology in the images obtained from IHC staining according to four types: rod (FIG. 10), rod cross-section (specifically referring to its circular cross-section scanned in the upright state of a rod HP, see FIG. 11), sphere (FIG. 10), and aggregation (FIG. 12). The sphere and rod cross-section are distinguished by the difference in diameter. Pathologically it is considered spherical when the diameter is 2-3 times the diameter of the neighboring rod.

Figure 13:
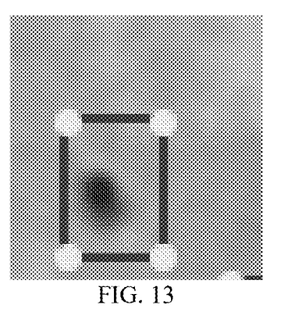
FIG. 13 is an electron micrograph of the HP intermediate morphology.

For the HP intermediate morphology (refer to the spherical deformation process of HP from rod to sphere, at that time, it is short and thick, see FIG. 13) and aggregation (refer to the aggregation of HP, which cannot clearly distinguish the morphology), we uniformly stipulate that the HP in the intermediate morphology is marked as a sphere because the pathologist will refer to the HP in the intermediate morphology for manual interpretation and include it in the final spherical deformation proportion. The HP in the aggregation state should be taken a single-layer picture when scanning, so that the subsequent machine learning can identify such aggregation, and the aggregation will not be included in the reference sphere deformation range in the pathology.

After labeling, a label file in xml format is generated, wherein the file contains the contents of label coordinate size, label type and picture information, and is constructed as a VOC2007 data file.

3. Image Preprocessing (1) Contrast enhancement: the problems of darkness and low contrast are common in immunochemical staining images, so HIS (Hue-Saturation-Intensity) color model and piecewise linear transformation can be used for contrast enhancement. Since the present invention is to process a true color image, a grayscale transformation method such as a piecewise linear transformation cannot be directly used, the original image is first transformed from an RGB color model to an HIS color model in which hue (H), saturation (S), and intensity (I) are separated, and a piecewise linear transformation method can be adopted for an intensity component (I).

Figure 4:
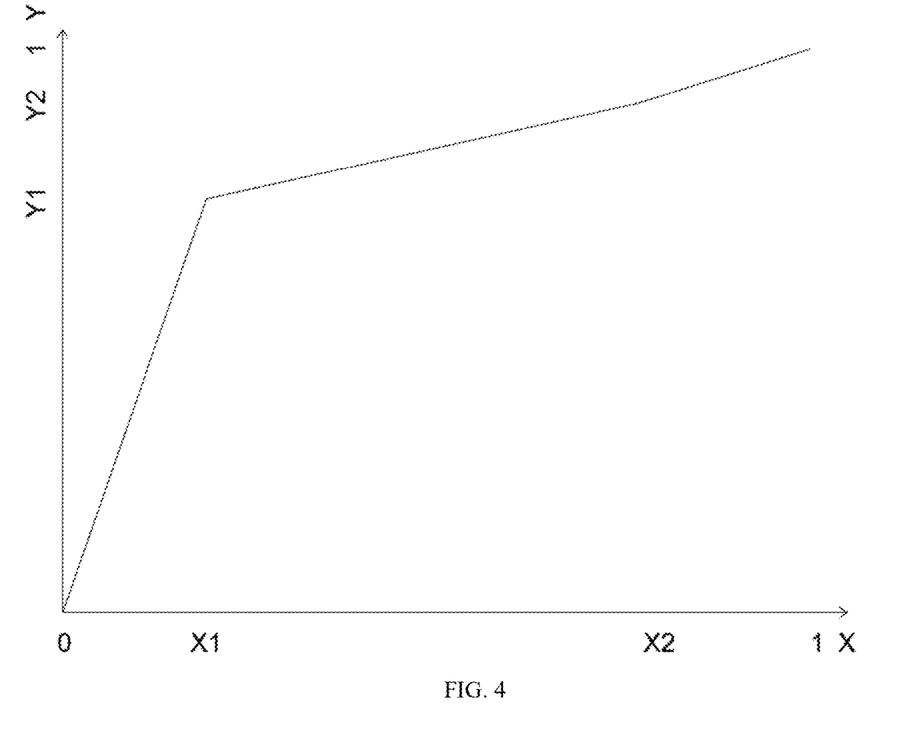
FIG. 4 shows an image hue color adjustment chart.

Piecewise linear transformation, also called grayscale stretch transformation, is a widely used way in image grayscale transformation. The piecewise linear transformation divides the gray-scale interval of an image into multiple pieces, and each linear transformation is respectively performed. Three pieces of linear transformation are very common. The advantage is that it can enhance the contrast of various parts of the original image, i.e., enhance the gray-scale regions of interest in the input image relative to those that are not of interest, and the form can be synthesized arbitrarily, which is very flexible. As shown in FIG. 4, X1, X2 gives the range of grey levels to be transformed, and Y1, Y2 determines the slope of the linear transformation, so the determination of the two pairs of turning points-(X1, Y1) and (X2, Y2) is the key point of the piecewise linear transformation. The abscissa in FIG. 4 represents the color hue saturation of the original image, the ordinate represents the color hue saturation of the adjusted image, and 0-1 is the range of values of X and Y.

On the original image, the pixel value of the point with the highest pixel value is max (possibly far from 1) and the pixel value of the point with the lowest pixel value is min (possibly far from 0). The linear transformation is to stretch the min (max) to (0, 1). In order to exclude bad points or pixel interference caused by the influence of noise, max takes 4-6% of the true maximum pixel value (namely, 4-6% of the pixel value of the point on the original image with the highest pixel value), and min takes 4-6% of the true minimum pixel value (namely, 4-6% of the pixel value of the point with the lowest pixel value). In this example, max takes 5% of the true maximum pixel value (i.e. 5% of the pixel value of the point on the artwork where the pixel value is the highest) and min takes 5% of the true minimum pixel value (i.e. 5% of the pixel value of the point where the pixel value is the lowest).

Linear transformation means that the transformation function is linear: Y=k (X−min) (Eq. 1-2), k=1/(max−min) (Eq. 1-1), k is the stretching coefficient, X is the color hue saturation of the original image, and Y is the ordinate representing the color hue saturation of the adjusted image.

A corresponding large amount of Y can be obtained after a large amount of X values are substituted into Eq. 1-2, and two pairs of turning points (X1, Y1) and (X2, Y2) of (0.25-0.32, 0.11-0.14) and (0.83-0.88, 0.90-0.99) are obtained by plotting X and Y as abscissa and ordinate, respectively.

The piecewise linear transformation can more flexibly control the distribution of the output gray histogram, and can selectively expand each piece of gray interval to improve the output image.

(2) Image filtering: the image filtering is to eliminate the noise in the image and keep the original details of the image as much as possible while suppressing the image noise. The present invention uses bilateral filtering techniques for image filtering. Bilateral filtering is a nonlinear filtering, in which the response value of pixel points is equal to the weighted average value of neighboring pixels. In the process of calculating the neighborhood weighting factor, the weighting coefficient of bilateral filtering is composed of the spatial proximity factor and gray similarity factor, which not only considers the distance factor but also uses the gray value similarity between neighboring pixels.

(3) HP staining extraction: immunochemical staining is rich in information, cytoplasm, nucleus and specific proteins are stained with different colors, which easily affect computer recognition. Therefore, according to the specific staining characteristics of HP by diaminobenzidine (DAB), using the improved deconvolution algorithm of the present invention, the DAB staining information is enhanced, other staining information is suppressed, and the morphological characteristics of HP are better preserved.

Color deconvolution performs normalized orthogonal transformation on an image according to the color space information of the image, and in each channel of RGB, each specific stain can be distinguished by a specific absorption factor C. According to Lambert-Beer's Law, the intensity $I_c$ of the light that can be transmitted has a direct exponential relationship with the staining amount A of the sample for a particular absorption factor C, which can be expressed as:

$$I_c = I_{o,c} \exp(-A * C_c) \quad \text{Eq. (2-1)}$$

Where, A represents the amount of stain applied, $I_{o,c}$ represents the intensity of incident light, $I_c$ represents the intensity of light after passing through the sample, and subscript c represents the channel of detection and $C_c$ represents the light absorption factor. It can be seen that the transmittance of light, the gray level per channel and the stain concentration are non-linear.

In the RGB mode, the intensity values of red, green, and blue light (denoted $I_r$, $I_g$, and $I_b$ respectively) are obtained from individual pixels of the camera. Because the staining amount and the concentration of colorant per channel are non-linear, the gray values of the three channels cannot be directly applied to the separation and measurement of each staining. However, the optical density (OD) of each channel can be defined as follows:

$$OD_c = -\log_{10}(I_c/I_{o,c}) = A*C_c \quad \text{Eq. (2-2)}$$

It can be seen that the optical density (OD) of each channel is linear with the staining amount A of the absorption factor and can therefore be used for separation of multiple staining of the sample.

The color deconvolution model is to transform an RGB image into a new space $\varphi_c'$ stained with stained tissue sections in the space $\varphi_c$. If a single picture is defined as a 2-dimensional form of $I=(F, \varphi)$, the pixel point F and the color space function pe associated with each pixel, the light density function of red, green and blue for each pixel, can be defined by Eq. (2-1) according to Lambert-Beer's law as:

$$\varphi_c = \exp(-S\varphi_c') \quad \text{Eq. (2-3)}$$

In addition, the relationship between $\varphi_c$ and $OD_c$ is: $\varphi_c = 10^{-OD_c}$ Eq. (2-5)

Where S is composed of the absorption factors corresponding to the three channels of RGB of each staining agent respectively, and the 3×3 matrix formed after the normalization treatment can be obtained to obtain a normalized matrix S:

|  | R | G | B |  |
|---|---|---|---|---|
| [ | $S_{r,1}$ | $S_{g,1}$ | $S_{b,1}$ | ] Hematoxylin |
|  | $S_{r,2}$ | $S_{g,2}$ | $S_{b,2}$ | Eosin |
|  | $S_{r,3}$ | $S_{g,3}$ | $S_{b,3}$ | DAB | transform Eq. (2-3) and Eq. (2-2) to obtain $$\varphi_c' = D\theta_c \quad \text{Eq. (2-4)}$$

Where D is the inverse matrix of S, $\theta_c = -\log(\varphi_c)$, and D is the obtained color deconvolution matrix.

Each particular stain has a corresponding optical density value in three RGB channels, which can be expressed as a 3×1 optical density (OD) vector. For example, if hematoxylin is used as a staining agent to pass through three channels R, G and B, respectively, the results according to the measured values are 0.18, 0.20 and 0.08, i.e. [0.18 0.20 0.08].

For example, if I is the image (F, $\varphi$) after mixed staining, the eigenvector [$A_{hematoxylin}$, $A_{cosin}$, $A_{DAB}$] of the image of the pixel in $\varphi'$ space of the image I is obtained according to the Eq. (2-4), and the following matrix is obtained through calculation:

Hematoxylin$_r$ eosin$_r$ DAB$_r$
Hematoxylin$_g$ eosin$_g$ DAB$_g$
Hematoxylin$_b$ eosin$_b$ DAB$_b$ Eq. (2-1) and the subsequent derived Eq. are adopted to correspondingly calculate the value of the corresponding component of the RGB space of the point, and the image is output so as to obtain three images contributing to the mixed image stained with different stains. Each pixel point is processed by the deconvolution algorithm and transformed into the grey levels according to the DAB staining amounts for subsequent labeling and modeling.

Figure 5:
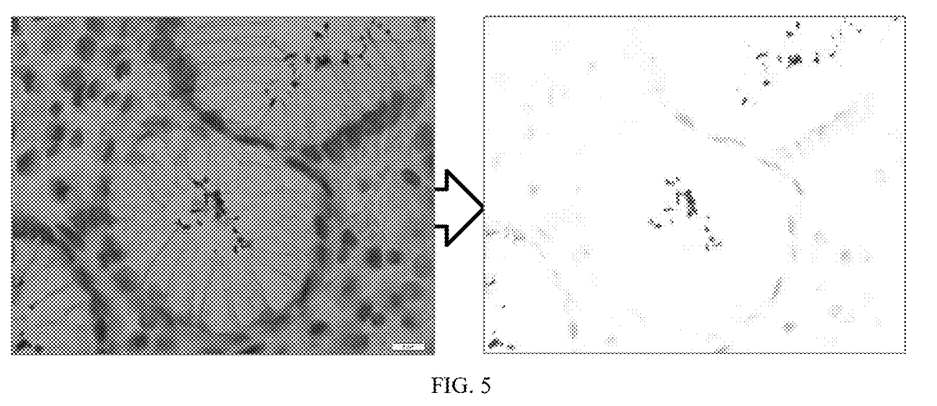
FIG. 5 shows a comparison before and after image preprocessing. To the left of the arrow is the image before processing, and to the right of the arrow is the processed image.

That is, in the case where S, A and $C_c$ are known, $OD_c$ is calculated by Eq. 2-2; $\varphi_c$ is calculated by Eq. 2-5; $\varphi_c'$ is calculated by Eq. 2-3; 0, is calculated by $\theta_c = -\log(\varphi_c)$; D is calculated by substituting $\varphi_c'$ and $\theta_c$ into Eqs. 2-4; and D is a 3×3 matrix composed of the staining amount of hematoxylin, eosin and DAB staining in an RGB space after the deconvolution algorithm; the image for AI identification can be obtained by taking the DAB staining amounts in the D matrix to transform to the gray levels (FIG. 5).

4. AI Modeling

Figure 6:
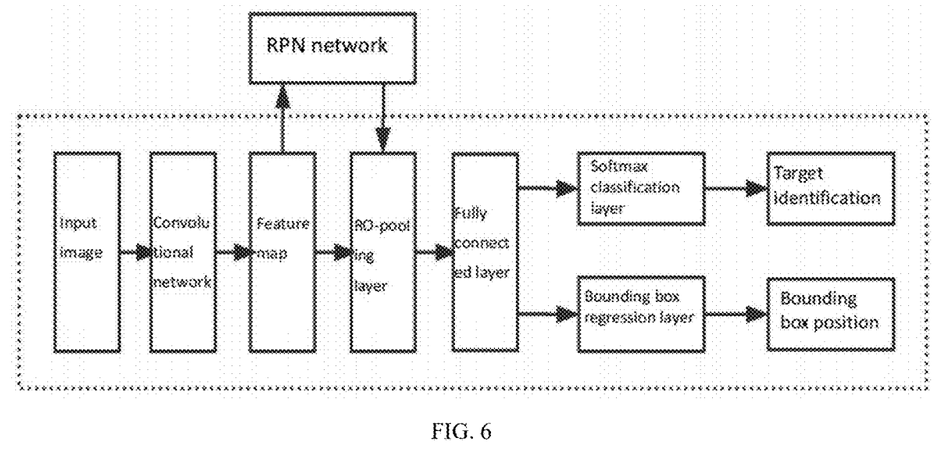
FIG. 6 is a schematic diagram of a Faster R-CNN network.

The present invention uses the Faster R-CNN algorithm for HP spherical deformation diagnosis model training. Faster R-CNN is a state-of-the-art object detection algorithm based on a deep learning network, which obtains several feature maps through the convolution layer and pooling layer in the convolution neural network, and then uses RPN (Region Proposal Network) to extract the region of interest. The ROI pooling layer then takes the region of interest and the convolved features as inputs and generates bounding boxes and corresponding class names for the object through the boundary regression layer and the softmax classification layer, respectively (FIG. 6).

Figure 7:
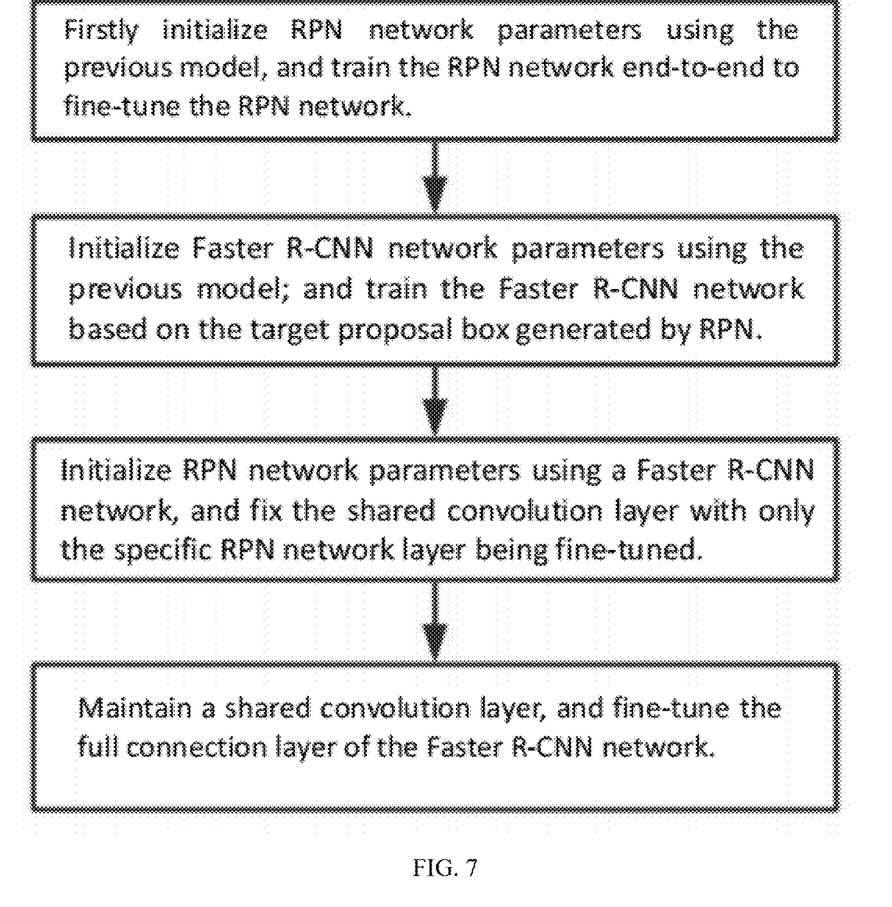
FIG. 7 is a flow chart of the Faster R-CNN alternating optimization training algorithm.

The present invention selects VGG16 as the underlying network model for Faster R-CNN. The VGG16 network model is obtained from the original author's pre-training of 1,280,000 images with 1,000 object classes, so this model can be used as a basis for training the HP spherical deformation diagnosis model based on the principle of transfer learning using a four-step algorithm of alternate optimization (FIG. 7). The four-step algorithm for alternate optimization includes: firstly initializing RPN network parameters using the VGG16 model, and training the RPN network end-to-end to fine-tune the RPN network; initializing the Faster R-CNN network parameters using the VGG16 model, and then training the Faster R-CNN network based on the target proposal box generated by RPN; then initializing RPN network parameters using a Faster R-CNN network, and fixing the shared convolution layer with only the specific RPN network layer being fine-tuned; finally maintaining a shared convolution layer, and fine-tuning the full connection layer of the Faster R-CNN network.

After model training, samples can be randomly divided into training sets and validation set according to the ratio of 9:1, and k-fold cross validation can be performed to further optimize the model. That is, the samples can be randomly divided into 10 groups for 10-fold cross-validation.

5. Software Identification and Reporting

Figure 8:
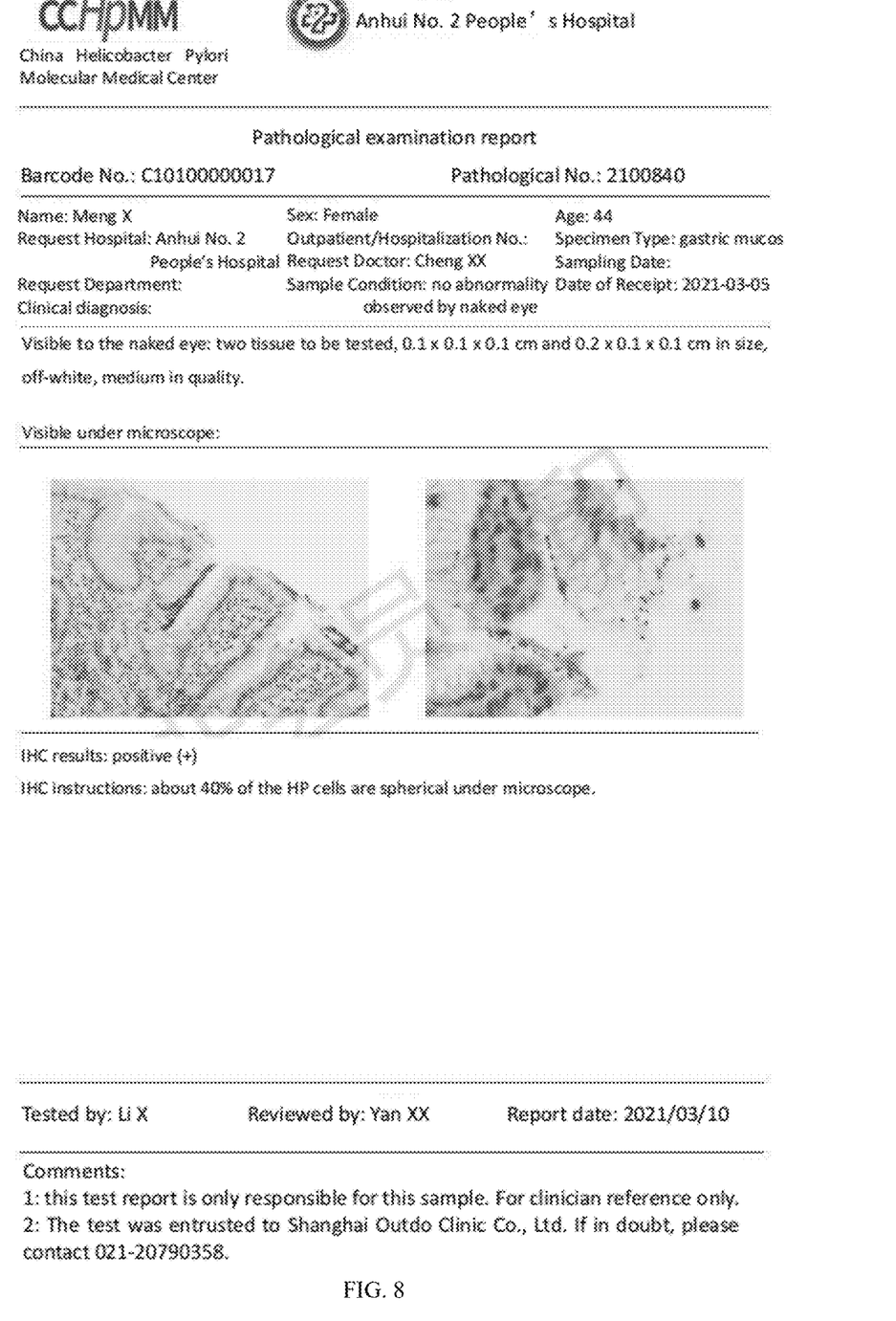
FIG. 8 is a diagram showing an example of a pathological examination report.

According to the above-mentioned model construction and training algorithm, HP identification can be performed automatically, so as to perform mapping and presentation of reporting results according to the reporting template conditions of various hospitals, so as to achieve an integrated reporting and issuing system. FIG. 8 is a pathological examination report issued when the HP spherical deformation diagnosis model according to the present invention is implemented in a hospital. It can be seen therefrom that the model can automatically identify whether the gastric mucosa sample contains HP, and how many proportions of the HP bacteria have spherical deformation.

Preferred specific embodiments of the present invention are described in detail above. It will be appreciated by persons skilled in the art that numerous modifications and variations can be made to the present invention without departing from the scope of the invention. Therefore, any technical solution that can be obtained by logical analysis, reasoning or limited experimentation by a person skilled in the art on the basis of the prior art in accordance with the concept of the present invention shall be within the scope determined by the claims.

What is claimed is:

1. A construction method for an HP spherical deformation diagnosis model, comprising steps of:
   S1, taking a plurality of immunochemical staining images having a *Helicobacter pylori* (HP) spherical deformation as a training set and a validation set respectively;
   S2, manually labeling a *Helicobacter pylori* morphology in the training set;
   S3, subjecting images in the training set to contrast enhancement, image filtering, and HP staining extraction operations; wherein the contrast enhancement comprises firstly transforming an original image from a red, green, blue (RGB) color model to a hue-intensity-saturation (HIS) color model, and a hue, a saturation, and an intensity are separated in the HIS color model, and then using a piecewise linear transformation method on a obtained brightness component; wherein the piecewise linear transformation method comprises substituting Eq. 1-1 into Eq. 1-2, in a case where X, min, and max are known, calculating Y to obtain a large number of Y corresponding to X, and plotting X and Y as horizontal and vertical coordinates to obtain two pairs of turning points (X1, Y1) and (X2, Y2); enhancing a grayscale region of interest in the original image by the piecewise linear transformation method, i.e. stretching to a (0, 1) interval, thereby improving the original image;

$$k=1/(\max-\min) \quad \text{Eq. 1-1}$$

$$Y=k(X-\min) \quad \text{Eq. 1-2}$$

wherein k is a stretching coefficient; max and min are 4-6% of a pixel value of a point with a highest pixel value on the original image and 4-6% of a pixel value of a point with a lowest pixel value on the original image, respectively; X is a color hue saturation of the original image;
   and Y is a color hue saturation of an adjusted image;
   the image filtering adopts a bilateral filtering technology to filter an improved image processed by the piecewise linear transformation method;
   the HP staining extraction adopts a deconvolution algorithm to enhance diaminobenzidine (DAB) staining information about the improved image after the image filtering, suppress other staining information, and transform the same into grey levels according to an amount of DAB staining, so as to obtain an image for an artificial intelligence (AI) identification;
   S4, training a U-Net neural network with the image for the AI identification;
   S5, performing a k-fold cross-validation and an optimization to obtain the HP spherical deformation diagnosis model;
   S6, performing an HP spherical deformation identification on an image in the validation set using the HP spherical deformation diagnosis model, and performing a consistency comparison with a manual interpretation result; wherein when a consistency reaches above 70%, the HP spherical deformation diagnosis model is successfully constructed;
   the deconvolution algorithm adopted in the step S3 is a color deconvolution technique, involving the following Eqs: Eq. 2-2, Eq. 2-3, Eq. 2-4, and Eq. 2-5;

$$OD_c=-\log_{10}(I_c/I_{o,c})=A \times C_c \quad \text{Eq. 2-2}$$

$$\varphi_c=\exp(-S\varphi_c') \quad \text{Eq. 2-3}$$

$$\varphi_c'=D\theta_c \quad \text{Eq. 2-4}$$

$$\varphi_c=10^{-ODc} \quad \text{Eq. 2-5}$$

wherein A represents an action amount of a stain; $I_{o,c}$ represents an intensity of an incident light; $I_c$ represents an intensity of a light after passing through a sample, and subscript c represents a detected channel; $C_c$ represents a light absorption factor; $OD_c$ represents an optical density; $\varphi_c$ represents a red, green, and blue optical density function of each pixel; $\varphi_c'$ represents a red, green, and blue optical density function of each pixel newly defined by staining with stained tissue sections; S represents a matrix composed of absorption factors respectively corresponding to three channels of RGB of each stain; and D is an inverse matrix of S; and $\theta_c=-\log(\varphi_c)$;
   in a case where S, A, and C, are known, $OD_c$ is calculated by Eq. 2-2; $\varphi_c$ is calculated by Eq. 2-5; $\varphi_c'$ is calculated by Eq. 2-3; $\theta_c$ is calculated by $\theta_c=-\log(\varphi_c)$; D is calculated by substituting $\varphi_c'$ and $\theta_c$ into Eq. 2-4;
   D is a 3×3 matrix composed of a staining amount of hematoxylin, eosin, and DAB staining in an RGB space after the deconvolution algorithm; a DAB staining amount in the D matrix is taken and transformed into a grey level to obtain the image for the AI identification; and
   the step S4 specifically comprises: training the U-Net neural network using a Faster region-based convolutional neural network (R-CNN) algorithm on the image for the AI identification; and adopting VGG16 as a base network model for the Faster R-CNN algorithm.

2. The construction method for the HP spherical deformation diagnosis model according to claim 1, wherein max and min are 5% of the pixel value of the point with the highest pixel value on the original image and 5% of the pixel value of the point with the lowest pixel value on the original image, respectively; X1 is 0.25-0.32; Y1 is 0.11-0.14; X2 is 0.83-0.88; and Y2 is 0.90-0.99.

3. The construction method for the HP spherical deformation diagnosis model according to claim 1, wherein each of the plurality of immunochemical staining images in the step S1 is one or more selected from the group consisting of an immunocytochemistry (ICC) staining image and an immunohistochemistry (IHC) staining image.

4. The construction method for the HP spherical deformation diagnosis model according to claim 3, wherein the step S2 specifically comprises: using LabelImg software to label the HP morphology in the ICC staining image and/or the IHC staining image according to four types: rod, rod cross-section, sphere, and aggregation, wherein a diameter of the sphere is 2-3 times a diameter of an adjacent rod, labeling all HP intermediate morphology as spherical wherein an HP intermediate morphology refers to a morphology of *Helicobacter pylori* during a deformation from the rod to the sphere; labeling the rod, the rod cross-section, and the aggregation as non-spherical wherein the aggregation means that HPs are aggregated together and the morphology cannot be clearly distinguished.

5. A construction system for an HP spherical deformation diagnosis model for identifying whether an HP spherical deformation exists in an IHC staining image of an HP positive gastric mucosal sample and/or an HP strain ICC staining image, comprising an image processing module and an identification module; wherein the image processing module comprises a contrast enhancement module, an image filtering module, and an HP staining extraction module;

the contrast enhancement module comprises:
an HIS color model transformation module configured to transform an original image from an RGB color model to an HIS color model, wherein a hue, a saturation, and an intensity are separated in the HIS color model; and
a piecewise linear transformation module configured to enhance a grayscale region of interest in the original image by using a piecewise linear transformation method for a brightness component in the HIS color module, so as to improve the original image;
wherein the piecewise linear transformation method comprises substituting Eq. 1-1 into Eq. 1-2, in a case where X, min, and max are known, calculating Y to obtain a large number of Y corresponding to X, and plotting X and Y as horizontal and vertical coordinates to obtain two pairs of turning points (X1, Y1) and (X2, Y2); enhancing the grayscale region of interest in the original image by the piecewise linear transformation method, i.e. stretching to a (0, 1) interval, thereby improving the original image;

$$k=1/(\text{max}-\text{min}) \quad \text{Eq. 1-1}$$

$$Y=k(X-\text{min}) \quad \text{Eq. 1-2}$$

wherein k is a stretching coefficient; max and min are 4-6% of a pixel value of a point with a highest pixel value on the original image and 4-6% of a pixel value of a point with a lowest pixel value on the original image, respectively; X is a color hue saturation of the original image; and Y is a color hue saturation of an adjusted image;

the image filtering module adopts a bilateral filtering technology to filter an improved image processed by the piecewise linear transformation method;

the HP staining extraction module adopts a deconvolution algorithm to enhance DAB staining information about the improved image after an image filtering processing, suppress other staining information, and transform the same into grey levels according to an amount of DAB staining, so as to obtain an image for an AI identification;

the deconvolution algorithm used by the HP staining extraction module is a color deconvolution technique, involving the following Eqs: Eq. 2-2, Eq. 2-3, Eq. 2-4, and Eq. 2-5;

$$OD_c=-\log_{10}(I_c/I_{o,c})=A\times C_c \quad \text{Eq. 2-2}$$

$$\varphi_c=\exp(-S\varphi_c') \quad \text{Eq. 2-3}$$

$$\varphi_c'=D\theta_c \quad \text{Eq. 2-4}$$

$$\varphi_c=10^{-OD_c} \quad \text{Eq. 2-5}$$

wherein A represents an action amount of a stain; $I_{o,c}$ represents an intensity of an incident light; $I_c$ represents an intensity of a light after passing through a sample, and subscript c represents a detected channel; $C_c$ represents a light absorption factor; $OD_c$ represents an optical density; $\varphi_c$ represents a red, green, and blue optical density function of each pixel; $\varphi_c'$ represents a red, green, and blue optical density function of each pixel newly defined by staining with stained tissue sections; S represents a matrix composed of absorption factors respectively corresponding to three channels of RGB of each stain; and D is an inverse matrix of S; and $\theta_c=-\log(\varphi_c)$;

in a case where S, A, and C, are known, $OD_c$ is calculated by Eq. 2-2; $\varphi_c$ is calculated by Eq. 2-5; $\varphi_c'$ is calculated by Eq. 2-3; $\theta_c$ is calculated by $\theta_c=-\log(\varphi_c)$; D is calculated by substituting $\varphi_c'$ and $\theta_c$ into Eq. 2-4;

D is a 3×3 matrix composed of a staining amount of hematoxylin, eosin, and DAB staining in an RGB space after the deconvolution algorithm; a DAB staining amount in the D matrix is taken and transformed into a grey level to obtain the image for the AI identification; and the identification module is configured to identify the image for the AI identification and make an interpretation of whether the HP spherical deformation exists, specifically comprising: training a U-Net neural network using a Faster R-CNN algorithm on the image for the AI identification; and adopting VGG16 as a base network model for the Faster R-CNN algorithm.

6. The construction system for the HP spherical deformation diagnosis model according to claim 5, wherein max and min are 5% of the pixel value of the point with the highest pixel value on the original image and 5% of the pixel value of the point with the lowest pixel value on the original image, respectively; X1 is 0.25-0.32; Y1 is 0.11-0.14; X2 is 0.83-0.88; and Y2 is 0.90-0.99.

7. The construction system for the HP spherical deformation diagnosis model according to claim 5, wherein the construction system is further configured to give a proportion of the IHC staining image of the HP positive gastric mucosal sample and/or the HP strain ICC staining image; the identification module, when identifying the image for the AI identification, is further configured for giving the proportion of the IHC staining image of the HP positive gastric mucosal sample and/or the HP strain ICC staining image.

8. A non-transitory computer-readable storage medium having stored thereon executable instructions that, when executed, implement the piecewise linear transformation module of the construction system for the HP spherical deformation diagnosis model according to claim 5.

9. The non-transitory computer-readable storage medium according to claim 8, wherein in the construction system for the HP spherical deformation diagnosis model, max and min are 5% of the pixel value of the point with the highest pixel value on the original image and 5% of the pixel value of the point with the lowest pixel value on the original image, respectively; X1 is 0.25-0.32; Y1 is 0.11-0.14; X2 is 0.83-0.88; and Y2 is 0.90-0.99.

10. The non-transitory computer-readable storage medium according to claim 8, wherein the construction system is further configured to give a proportion of the IHC staining image of the HP positive gastric mucosal sample and/or the HP strain ICC staining image; the identification module, when identifying the image for the AI identification, is further configured for giving the proportion of the IHC staining image of the HP positive gastric mucosal sample and/or the HP strain ICC staining image.

11. A terminal, comprising:
a memory configured to store executable instructions;
a processor configured to, when executing the executable instructions stored in the memory, implement the piecewise linear transformation module of the construction system for the HP spherical deformation diagnosis model according to claim 5.

12. The terminal according to claim 11, wherein in the construction system for the HP spherical deformation diagnosis model, max and min are 5% of the pixel value of the point with the highest pixel value on the original image and 5% of the pixel value of the point with the lowest pixel value on the original image, respectively; X1 is 0.25-0.32; Y1 is 0.11-0.14; X2 is 0.83-0.88; and Y2 is 0.90-0.99.

13. The terminal according to claim 11, wherein the construction system is further configured to give a proportion of the IHC staining image of the HP positive gastric mucosal sample and/or the HP strain ICC staining image; the identification module, when identifying the image for the AI identification, is further configured for giving the proportion of the IHC staining image of the HP positive gastric mucosal sample and/or the HP strain ICC staining image.

* * * * *